United States Patent [19]

Meyer et al.

[11] 4,425,154
[45] Jan. 10, 1984

[54] N-PHENYLSULFONYL-N'-PYRIMIDINYLUREAS

[75] Inventors: Willy Meyer, Riehen; Werner Föry, Basel, both of Switzerland

[73] Assignee: Ciba-Geigy Corporation, Ardsley, N.Y.

[21] Appl. No.: 458,696

[22] Filed: Jan. 17, 1983

Related U.S. Application Data

[60] Continuation-in-part of Ser. No. 417,716, Sep. 13, 1982, abandoned, which is a division of Ser. No. 282,847, Jul. 13, 1981.

[30] Foreign Application Priority Data

Jul. 17, 1980 [CH] Switzerland .................. 5481/80
Nov. 5, 1980 [CH] Switzerland .................. 8216/80
Jun. 17, 1981 [CH] Switzerland .................. 3991/81

[51] Int. Cl.³ .................. C07D 239/42; A01N 43/54
[52] U.S. Cl. .................. 71/92; 544/321; 544/332
[58] Field of Search .................. 544/321, 332; 71/92

[56] References Cited

U.S. PATENT DOCUMENTS 4,310,346 1/1982 Levitt .................. 71/92

FOREIGN PATENT DOCUMENTS 23422 2/1981 European Pat. Off. .................. 71/92
46677 3/1982 European Pat. Off. .................. 71/92

Primary Examiner—Robert Gerstl
Attorney, Agent, or Firm—Frederick H. Rabin; Bruce M. Collins

[57] ABSTRACT

N-Phenylsulfonyl-N'-pyrimidinyl ureas of the formula

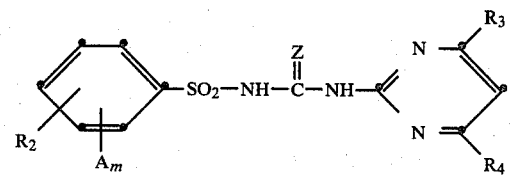

and the salts thereof with amines, alkali metal or alkaline earth metal bases or with quaternary ammonium bases, have good pre- and postemergence selective herbicidal and growth regulating properties. In the above formula A is a $C_2$–$C_6$ alkenyloxy, $C_2$–$C_6$ haloalkenyloxy, $C_2$–$C_6$ haloalkenylthio, $C_2$–$C_6$ haloalkenylsulfinyl or $C_2$–$C_6$ haloalkenylsulfonyl radical Z is oxygen or sulfur, m is 1 or 2, $R_2$ is hydrogen, halogen, $C_1$–$C_5$alkyl, $C_2$–$C_5$alkenyl, $C_1$–$C_4$haloalkyl, or a radical —Y—$R_5$, —COO$R_6$, —NO$_2$ or —CO—N$R_7$—$R_8$, $R_3$ and $R_4$, each independently of the other, are hydrogen, $C_1$–$C_4$alkyl, $C_1$–$C_4$alkoxy, $C_1$–$C_4$alkylthio, $C_1$–$C_4$haloalkyl, halogen or alkoxyalkyl of at most 4 carbon atoms, $R_5$ and $R_6$, each independently of the other, are $C_1$–$C_5$alkyl, $C_2$–$C_5$alkenyl or $C_2$–$C_6$alkynyl, $R_7$ and $R_8$, each independently of the other, are hydrogen, $C_1$–$C_5$alkyl, $C_2$–$C_5$alkenyl or $C_2$–$C_6$alkynyl, and Y is oxygen, sulfur, a sulfinyl or sulfonyl bridge.

24 Claims, No Drawings

N-PHENYLSULFONYL-N'-PYRIMIDINYLUREAS

CROSS REFERENCE TO RELATED APPLICATIONS

This is a continuation-in-part of application Ser. No. 417 716 filed Sept. 13, 1982 abandoned which in turn is a divisional of application Ser. No. 282 847 filed July 31, 1981.

The present invention relates to novel N-phenylsulfonyl-N'-pyrimidinyl ureas having herbicidal and plant growth-regulating properties, to the production thereof, to composition containing them, and to the use thereof for controlling weeds, in particular selectively, in crops of useful plants, or for regulating and inhibiting plant growth.

The N-phenylsulfonyl-N'-pyrimidinyl ureas of this invention have the general formula I

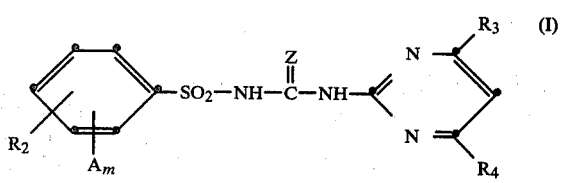

wherein

A is a $C_2$–$C_6$ alkenyloxy, $C_2$–$C_6$ haloalkenyloxy, $C_2$–$C_6$ haloalkenylthio, $C_2$–$C_6$ haloalkenylsulfinyl or $C_2$–$C_6$ haloalkenylsulfonyl radical Z is oxygen or sulfur, m is 1 or 2, $R_2$ is hydrogen, halogen, $C_1$–$C_5$alkyl, $C_2$–$C_5$alkenyl, $C_1$–$C_4$-haloalkyl, or a radical —Y—$R_5$, —COO$R_6$, —$NO_2$ or —CO—$NR_7$—$R_8$, $R_3$ and $R_4$, each independently of the other, are hydrogen, $C_1$–$C_4$alkyl, $C_1$–$C_4$alkoxy, $C_1$–$C_4$alkylthio, $C_1$–$C_4$haloalkyl, halogen or alkoxyalkyl of at most 4 carbon atoms, $R_5$ and $R_6$, each independently of the other, are $C_1$–$C_5$alkyl, $C_2$–$C_5$alkenyl or $C_2$–$C_6$alkynyl, $R_7$ and $R_8$, each independently of the other, are hydrogen, $C_1$–$C_5$alkyl, $C_2$–$C_5$alkenyl or $C_2$–$C_6$alkynyl, and Y is oxygen, sulfur, a sulfinyl or sulfonyl bridge, and salts of these compounds.

Herbicidally active ureas, triazines and pyrimidines are generally known in the art. Arylsulfamoyl-heterocyclylaminocarbamoyl compounds with herbicidal and plant growth-regulating action have recently been described, for example in European patent publication Nos. 1514 and 1515, U.S. Pat. No. 4,127,405, German Offenlegungsschrift No. 2 715 786 or French patent specification No. 1 468 747.

In the above definitions, alkyl denotes straight-chain or branched alkyl, e.g. methyl, ethyl, n-propyl, isopropyl, the four isomers of butyl, n-amyl, isoamyl, 2-amyl, 3-amyl, n-hexyl or isohexyl, with straight-chain alkyl being preferred.

Alkoxy denotes methoxy, ethoxy, n-propyloxy, isopropoxy and the four butyloxy isomers, and is, in particular, methoxy or ethoxy.

Alkylthio is e.g. methylthio, ethylthio, n-propylthio, isopropylthio and n-butylthio, with methylthio and ethylthio being preferred.

Examples of alkenyl radicals are vinyl, allyl, isopropenyl, 1-propenyl, 1-butenyl, 2-butenyl, 3-butenyl, 1-isobutenyl, 2-isobutenyl, 1-pentenyl, 2-pentenyl, 3-pentenyl and 4-pentenyl, with vinyl, allyl and 4-pentenyl being preferred.

Alkylsulfinyl is e.g. methylsufinyl, ethylsulfinyl, n-propylsulfinyl and n-butylsulfinyl, with methylsulfinyl and ethylsulfinyl being preferred.

Alkylsulfonyl is e.g. methylsulfonyl, ethylsulfonyl, n-propylsulfonyl and n-butylsulfonyl, with methylsulfonyl and ethylsulfonyl being preferred.

Halogen in the definitions of $R_1$ to $R_4$ and in haloalkoxy, haloalkylsulfinyl, haloalkylsulfonyl, haloalkylthio and haloalkenyl is fluorine, chlorine and bromine, with fluorine and chlorine being preferred.

The invention also comprises the salts which the compounds of formula I are able to form with amines, alkali metal and alkaline earth metal bases or quaternary ammonium bases.

Preferred salt-forming alkali metal and alkaline earth metal hydroxides are the hydroxides of lithium, sodium, potassium, magnesium or calcium, most preferably of sodium or potassium.

Examples of suitable salt-forming amines are primary, secondary and tertiary aliphatic and aromatic amines such as methylamine, ethylamine, propylamine, isopropylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Preferred compounds of the formula I are those in which (a) Z is oxygen and (b) $R_3$ and $R_4$ together contain not more than 4 carbon atoms.

Group (a) can be divided into two further subgroups which consist of compounds in which (aa) m is 1, and (ab) m is 2.

Preferred compounds in group (aa) are those in which the radical —A is in the 2- or 3-position to the sulfonyl radical. Among these preferred compounds further preference attaches to those compounds in which the radical —A is in the 2-position.

A preferred group of compounds in group (ab) comprises those compounds in which both radicals —A are in the 2 and 5-position to the sulfonyl group.

A further preference in connection with compounds of the above subgroups (aa) and (ab) consists in the feature that the radicals $R_3$ and $R_4$ together contain at most 4 carbon atoms. Accordingly, particularly preferred groups of compounds of formula I are the groups (aab) in which only one radical —A is in the 2-position to the sulfonyl radical, Z is oxygen and $R_3$ and $R_4$ together contain not more than 4 carbon atoms, and (abb) in which two radicals —A are in the 2- and 5-position to the sulfonyl radical, Z is oxygen and $R_3$ and $R_4$ together contain not more than 4 carbon atoms.

Preferred compounds of the group (aab) are those in which $R_2$ is in the 5- or 6-position to the sulfonyl group. Among these preferred compounds, preference attaches in turn to those compound in which $R_2$ is hydrogen, halogen, $C_1$–$C_4$alkoxy, nitro or $COOR_6$.

Further preferred compounds within this last mentioned group are those in which $R_2$ is hydrogen, fluorine, nitro or $C_1$–$C_4$alkoxy, and each of $R_3$ and $R_4$ is hydrogen, $C_1$–$C_4$alkyl, $C_1$–$C_4$alkoxy, $C_1$–$C_4$alkylthio, halogen or alkoxyalkyl, whilst $R_3$ and $R_4$ together contain at most 4 carbon atoms.

Among these compounds, preferred compounds are in turn those in which $R_2$ is hydrogen and each of $R_3$ and $R_4$ is $C_1$–$C_4$alkyl, $C_1$–$C_4$alkoxy, methylthio, halogen or alkoxyalkyl.

Of these compounds, the most preferred are in turn those in which A is $C_2$–$C_4$haloalkenyloxy or $C_2$–$C_6$-alkenyloxy.

Two preferred subgroups of compounds belonging to this last group are those in which ($\alpha$) A is $C_2$–$C_6$alkenyloxy and each of $R_3$ and $R_4$ is methyl, ethyl, chlorine or methoxy, and ($\beta$) A is vinyloxy substituted by 1 to 3 halogen atoms and each of $R_3$ and $R_4$ is methyl, ethyl, chlorine or methoxy.

Of the compounds of formula I in which Z is sulfur, those compounds are preferred in which $R_3$ and $R_4$, each independently of the other, are $C_1$–$C_3$alkyl, $C_1$–$C_3$alkoxy or $C_1$–$C_3$alkylthio, containing together at most 4 carbon atoms, and A is —O—CCl=CHCl and the radical —A is in the 2-position and m is 1.

A preferred individual compound is N-[2-(1,2-dichlorovinyloxy)-phenylsulfonyl]-N'-(4-chloro-6-methoxy-pyrimidin-2-yl) urea.

The process for obtaining the compounds of formula I is carried out in an inert organic solvent.

In a first process, the compounds of the formula I are obtained by reacting a phenylsulfonamide of the formula II

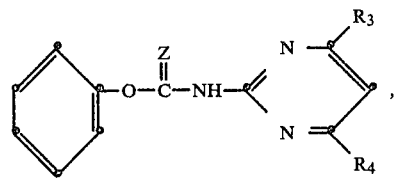
(II)

wherein A, $R_2$ and m are as defined for formula I, in the presence of a base, with a N-pyrimidinyl-carbamate of the formula III

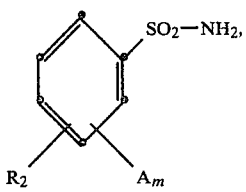
(III)

wherein $R_3$, $R_4$ and Z are as defined for formula I.

In a second process, compounds of formula I are obtained by reacting a phenylsulfonylisocyanate or phenylsulfonylisothiocyanate of the formula IV

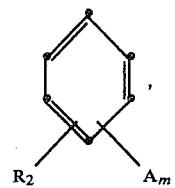
(IV)

wherein A, $R_2$, m and Z are as defined for formula I, optionally in the presence of a base, with an amine of the formula V

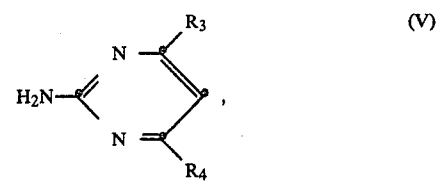
(V)

wherein $R_3$ and $R_4$ are as defined for formula I.

In a further process, the compounds of formula I are obtained by reacting a sulfonamide of the formula II above, optionally in the presence of a base, with an isocyanate or isothiocyanate of the formula VI

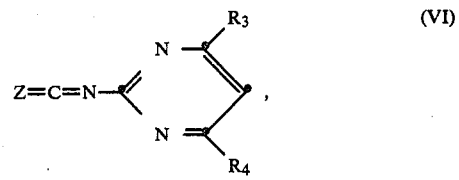
(VI)

wherein $R_3$, $R_4$ and Z are as defined for formula I.

Finally, the compounds of formula I can also be obtained by reacting a N-phenylsulfonylcarbamate of the formula VII

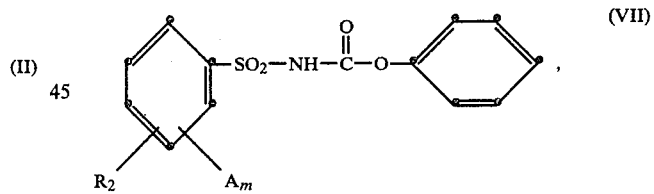
(VII)

wherein A, $R_2$ and m are as defined for formula I, with an amine of the formula V above.

If desired, the ureas of formula I can be converted into salts with amines, alkali metal or alkaline earth metal hydroxides or quaternary ammonium bases. This conversion is carried out e.g. by reacting the compounds of formula I with the equimolar amount of a base and removing the solvent by evaporation.

Some of the starting materials of the formulae II, IV and VII are novel and can be prepared by the following methods.

The novel sulfonamides of formula II used as intermediates are obtained from the corresponding anilines by diazotisation and replacement of the diazo group, with sulfur dioxide, in the presence of a catalyst such as copper(I) chloride, in hydrochloric acid or acetic acid, and reacting the resultant phenylsulfonyl chloride with ammonium hydroxide solution.

The compounds of formula II can also be obtained by O- or S-alkenylation of hydroxy- or thiophenylsulfonamides with the corresponding halides or sulfuric acid esters, or by reaction of ortho-halophenyl-sulfonamides with metal alcoholates or mercaptides and, if desired, by oxidation thereof e.g. with periodates or peracids to give the corresponding sulfoxides and sulfones.

Ortho-hydroxyphenylsulfonamides or substituted ortho-hydroxyphenylsulfonamides of the formula VIII

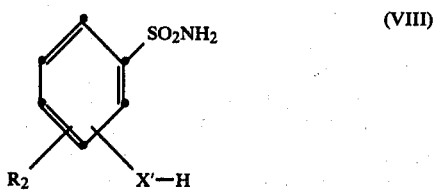

wherein $R_2$ is as defined for formula I and X' is oxygen or sulfur, as starting materials of specific sulfonamides of the formula II, are novel, with the exception of ortho-hydroxyphenylsulfonamide. They can be obtained by ether cleavage of corresponding $C_1$-$C_4$alkoxyphenylsulfonamides, e.g. with boron trihalides [such reactions are described in U.S. Pat. No. 3,904,680 and in J.Am.Chem. Soc., 64, 1128 (1942)] or by hydrogenolysis of the corresponding benzylphenylsulfonamides, as described in J. Chem. Soc. 1958, 2903.

The alkoxyphenylsulfonamides can, in turn, be obtained from the corresponding alkoxyanilides, as already mentioned, or by chlorosulfonylation of alkoxybenzenes and reaction of the resultant phenylsulfonyl chlorides with ammonium hydroxide solution. Such reactions are known from from J. Am. Chem. Soc. 62, 603 (1940).

The phenylsulfonylisocyanates of the formula IV can be obtained by reacting the sulfonamides of the formula II with phosgene, in the presence of butylisocyanate in a chlorinated hydrocarbon as solvent, at reflux temperature. Similar reactions are described in "Newer Methods of Preparative Organic Chemistry", Vol. VI, 223–241, Academic Press, New York and London.

The isothiocyanates of the formula IV are obtained by treating the sulfonamides of formula II with carbon disulfide and potassium hydroxide and by subsequent reaction of the dipotassium salt with phosgene. Such processes are described in Arch. Pharm. 299, 174 (1966).

The N-phenylsulfonylcarbamates of the formula VII are obtained by reacting the sulfonamides of the formula II with diphenyl carbonate in the presence of a base. Similar processes are described in Japanese patent specification No. 61 169.

The starting materials of the formulae III, V and VI are known or they can be prepared by known methods.

Isocyanates of the formula VI can be prepared by reacting amines of the formula V with oxalyl chloride in a chlorinated hydrocarbon as solvent. Amines of the formula V are known and some are commercially available, or they can be prepared by known methods, q.v. "The Chemistry of Heterocyclic Compounds", Vol. XIV, Interscience Publishers, New York, London.

It is expedient to carry out the reactions for obtaining compounds of formula I in aprotic, inert organic solvents such as methylene chloride, tetrahydrofurane, acetonitrile, dioxane or toluene.

The reaction temperatures are preferably in the range from $-20°$ and $+120°$ C. The reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst.

The final products can be isolated by concentrating the reaction mixture and/or removing the solvent by evaporation, and by recrystallisation or by triturating the solid residue in solvents in which it is poorly soluble, such as ether, aromatic hydrocarbons or chlorinated hydrocarbons.

The compounds of formula I are stable compounds, and no protective measures are required for handling them.

The compounds of formula I have pronounced plant growth-regulating, especially plant growth-inhibiting, properties. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Further, the compounds of formula I are suitable for preventing stored potatoes from seeding. During winter storage, potatoes often develop sprouts which result in shrinkage, weight loss, and rot.

When the compounds of formula I are applied in higher rates of application, all tested plants are so damaged in their development that they wither. When used in lower rates of application, the compounds of formula I have good selective growth-inhibiting and selectve herbicidal properties which make them most suitable for use in crops of useful plants, especially in cereals, cotton, soybeans, maize and rice. In some cases damage is also caused to weeds which have up to now have only been controlled with total herbicides.

The mode of action of these compounds is unusual. Many are translocatable, i.e. they are absorbed by the plant and transported to other parts of it where they then deploy their action. The unusual feature of the compounds is that they do not only take the path through the vascular bundle in the ligneous part from the roots to the leaves, but can also be translocated through the sieve tubes in the bast part of the leaves back into the roots. Thus, for example, it is possible to damage perennial weeds to the very roots by surface treatment. Compared with other herbicides and growth regulators, the novel compounds of the formula I are effective even when used in very low rates of application.

The invention also relates to herbicidal and plant growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or preferably together with the adjuvants conventionally employed in the art of formulation, and are therefore formulated in known manner to emulsifible concentrates, directly sprayable or dilutable solutions, dilute emulsions, wettable powders, soluble powders, dusts, granulates, and also encapsulations in e.g. polymer substances. The methods of application, such as spraying, atomising, dusting, scattering or pouring, are chosen in accordance with the intended objectives and the prevailing circumstances, just like the nature of the compositions.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali, alkaline earth or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfonates, sulfonated benzimidazole derivatives or alkylarylsulfonates.

The fatty sulfonates or sulfates are usually in the form of alkali, alkaline earth or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminepolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol-polyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one polyglycol ether or $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp., Ridgewood, New Jersey, 1979; Sisley and Wood, "Encyclopedia of Surface Active Agents", Chemical Publishing Co. Inc., New York, 1964.

The pesticidal formulations usually contain 0.1 to 95%, preferably 0.1 to 80%, of a compound of the formula I, 1 to 99.9% of a solid or liquid adjuvant, and 0 to 25%, preferably 0.1 to 25%, of a surfactant.

Preferred formulations are composed in particular of the following constituents (%=percentage by weight):

| Solutions | |
| --- | --- |
| active ingredient: | 1 to 30%, preferably 5 to 20% |
| solvent: | 99 to 0%, preferably 95 to 0% |
| surfactants: | 1 to 99%, preferably 0 to 95% |
| Emulsifiable concentrates | |
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 90 to 30% |
| surfactant: | 1 to 40%, preferably 2 to 30% |
| Wettable powders | |
| active ingredient: | 0.5 to 90%, preferably 1 to 80% |

-continued

| | |
|---|---|
| surfactant: | 0.5 to 20%, preferably 1 to 15% |
| solid carrier: | 5 to 95%, preferably 15 to 90% |

Granulates

| | |
|---|---|
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001%. The rates of application are normally 0.01 to 10 kg a.i./ha, preferably 0.025 to 5 kg a.i./ha.

The compositions can also contain further ingredients such as stabilisers, antifoams, viscosity regulators, binders, adhesives, as well as fertilisers or other active compounds, in order to attain special effects.

PREPARATORY EXAMPLES

EXAMPLE 1

2-Hydroxyphenylsulfonamide 22.2 ml of boron tribromide are added dropwise, under nitrogen and at room temperature, over 15 minutes to a suspension of 39 g of 2-methoxyphenylsulfonamide in 210 ml of dry methylene chloride. The reaction mixture is then stirred for 1 hour at room temperature. After the mixture has been cooled to 0° C., 200 ml of methanol are added over 15 minutes and the clear solution is concentrated. The oily residue is taken up in ethyl acetate and the solution is washed twice with water, dried over sodium sulfate, and evaporated to dryness. The residue is triturated with petroleum ether, affording 25.1 g of 2-hydroxyphenylsulfonamide with a melting point of 136°–138° C.

The hydroxyphenylsulfonamides of the formula VIII listed in the following Table 1 are obtained in analogous manner:

TABLE 1

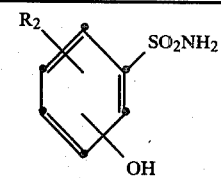

| $R_2$ | Position of —OH | Physical data (°C.) |
|---|---|---|
| 5-$C_3H_7$—i | 2 | m.p. 90–91° |
| 2-$CH_3$ | 5 | |
| 2-Cl | 5 | |
| 5-F | 2 | m.p. 141–142° |
| 5-Br | 2 | m.p. 169–70° |
| 5-$NO_2$ | 2 | m.p. 180–185° |
| 3-$CH_3$ | 2 | m.p. 133–134° |
| 2-$CH_3$ | 3 | |
| 3-Cl | 2 | |
| 6-$CH_3$ | 2 | |
| 3-$OCH_3$ | 2 | |
| 2-$OCH_3$ | 3 | |
| 6-$OCH_3$ | 2 | |
| 6-OH | 2 | |
| 5-$OCH_3$ | 2 | m.p. 119–20° |
| 2-$OCH_3$ | 5 | m.p. 213–15° |
| 5-$CH_3$ | 2 | m.p. 155–156° |
| 6-Cl | 2 | m.p. 190–91° |
| 3-$NO_2$ | 2 | |

TABLE 1-continued

| $R_2$ | Position of —OH | Physical data (°C.) |
|---|---|---|
| 3-$COOCH_3$ | 2 | |
| 5-$COOCH_3$ | 2 | m.p. 171–172° |
| 5-Cl | 2 | m.p. 176–179° |
| 3-$NH_2$ | 2 | |
| 5-$NH_2$ | 2 | |
| 5-$CON(CH_3)_2$ | 2 | |
| 6-$NO_2$ | 2 | |
| 6-$COOCH_3$ | 2 | |

EXAMPLE 2

2-Allyloxyphenylsulfonamide

A mixture of 3.5 g of 2-hydroxyphenylsulfonamide, 5.5 g of potassium carbonate and 1.7 ml of allyl bromide in 100 ml of methyl ethyl ketone is stirred, under nitrogen, for 1 hour at reflux temperature. The reaction mixture is cooled to room temperature, filtered, and evaporated to dryness. Once recrystallisation from ethyl acetate yields 3.27 g of 2-allyloxyphenylsulfonamide with a melting point of 104°–105° C.

Sulfonamides of the formula II which can be obtained in analogous manner are listed in Table 2.

EXAMPLE 3

(a) 2-(1,2-Dichlorovinyloxy)-phenylsulfonylchloride 21 ml of a 40% aqueous solution of sodium hydrogensulfite are added dropwise with cooling to a solution of 3 g copper sulfate pentahydrate in 90 ml of 32% hydrochloric acid. To the obtained suspension at a temperature of 10°–15° C. simultaneously are added dropwise 21 ml of a 40% solution of sodium hydrogensulfite and a cooled solution of 2-(1,2-dichlorovinyloxy)-aniline diazonium salt, which solution can be obtained by adding dropwise at a temperature of 0°–5° C. a solution of 6.9 g sodium nitrite in 10 ml of water to a suspension of 24 g of 2-(1,2-dichlorovinyloxy)-aniline, 50 ml of water and 15 ml of 32% hydrochloric acid. The reaction mixture is stirred for 16 hours, extracted with methylene chloride, dried and evaporated to dryness, yielding 17.5 g of 2-(1,2-dichlorovinyloxy)phenylsulfonyl-chloride.

(b) 2-(1,2-Dichlorovinyloxy)-phenylsulfonamide

A solution of 17.5 g of 2-(1,2-dichlorovinyloxy)-phenylsulfonyl-chloride in 150 ml of methylene chloride is added slowly to a mixture of 30 ml of methylene chloride, 50 ml of water and 50 ml of 30% aqueous ammonia. The reaction mixture is stirred for 6 hours at a temperature of 20°–25° C. The organic phase is washed with water, dried over sodium sulfate and evaporated to a volume of 40 ml. The crystallised 2-(1,2-dichlorovinyloxy)phenylsulfonamide is separated and dried. Yield: 12.5 g, m.p. 147°–149° C.

Sulfonamides of the formula II which can be obtained in analogous manner are listed in Table 2.

TABLE 2

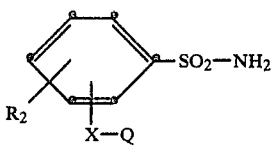

| $R_2$ | X | Q | Position of —X—Q | Physical data (°C.) |
|---|---|---|---|---|
| H | O | —CCl=CHCl | 2 | m.p. 147–149° |
| H | S | —CCl=CHCl | 2 | |
| H | SO | —CCl=CHCl | 2 | |
| H | $SO_2$ | —CCl=CHCl | 2 | |
| H | O | —CH=$CCl_2$ | 2 | |
| H | S | —CH=$CCl_2$ | 2 | |
| H | SO | —CH=$CCl_2$ | 2 | |
| H | $SO_2$ | —CH=$CCl_2$ | 2 | |
| H | O | —$CH_2CH$=$CH_2$ | 2 | m.p. 104–5° |
| H | O | —$CH_2$—C($CH_3$)=$CH_2$ | 2 | m.p. 104–105° |
| H | O | —$(CH_2)_2$—CH=$CH_2$ | 2 | |
| H | O | —$(CH_2)_3$—CH=$CH_2$ | 2 | |
| H | O | —$CH_2$—CH=C$(CH_3)_2$ | 2 | |
| H | O | —$CH_2$—CH=CH—$CH_3$ | 2 | m.p. 113–114° |
| H | O | —CH($CH_3$)—CH=$CH_2$ | 2 | |
| 6-Cl | O | —$CH_2CH$=$CH_2$ | 2 | m.p. 127–128° |
| 6-Cl | O | —$CH_2$—C($CH_3$)=$CH_2$ | 2 | |
| 6-Cl | O | —$CH_2$—CH=$(CH_3)_2$ | 2 | |
| 6-Cl | O | —$CH_2$—CH=CH—$CH_3$ | 2 | |
| 6-$OCH_3$ | O | —$CH_2$—CH=$CH_2$ | 2 | |
| 6-$OCH_3$ | O | —$CH_2$—C($CH_3$)=$CH_2$ | 2 | |
| 6-$OCH_3$ | O | —$CH_2$—CH=C$(CH_3)_2$ | 2 | |
| 6-$OCH_3$ | O | —$(CH_2)_2$—CH=$CH_2$ | 2 | |
| 6-$CH_3$ | O | —$CH_2CH$=$CH_2$ | 2 | |
| 6-$CH_3$ | O | —$CH_2$—C($CH_3$)=$CH_2$ | 2 | |
| 6-$NO_2$ | O | —$CH_2$—CH=$CH_2$ | 2 | |
| 6-$NO_2$ | O | —$CH_2$—CH=CH—$CH_3$ | 2 | |
| 6-$NO_2$ | O | —$CH_2$—C($CH_3$)=$CH_2$ | 2 | |
| 6-$COOCH_3$ | O | —$CH_2$—CH=$CH_2$ | 2 | |
| 5-Cl | O | —$CH_2$—CH=$CH_2$ | 2 | m.p. 122° |
| 5-Cl | O | —$CH_2$—C($CH_3$)=$CH_2$ | 2 | |
| 5-Br | O | —$CH_2$—C($CH_3$)=$CH_2$ | 2 | |
| 5-Br | O | —$CH_2$—CH=$CH_2$ | 2 | m.p. 110–111° |
| 5-F | O | —$CH_2$—CH=$CH_2$ | 2 | m.p. 113–114 |
| 5-F | O | —$CH_2$—CH=C$(CH_3)_2$ | 2 | |
| 5-$C_3H_7$—i | O | —$CH_2$—CH=C$(CH_3)_2$ | 2 | |
| 5-$C_3H_7$—i | O | —$CH_2$—CH=$CH_2$ | 2 | oil |
| 5-$CH_3$ | O | —$CH_2$—CH=$CH_2$ | 2 | m.p. 139–140° |
| 5-$CH_3$ | O | —$CH_2$—CH=CH—$CH_3$ | 2 | |
| 5-$NO_2$ | O | —$CH_2$—CH=CH—$CH_3$ | 2 | |
| 5-$NO_2$ | O | —$CH_2CH$=$CH_2$ | 2 | m.p. 139–141° |
| 5-$OCH_3$ | O | —$CH_2CH$=$CH_2$ | 2 | m.p. 88–89° |
| 5-$OCH_3$ | O | —$CH_2$—C($CH_3$)=$CH_2$ | 2 | |
| 5-$OCH_3$ | O | —$CH_2$—CH=CH—$CH_3$ | 2 | |
| 5-CON$(CH_3)_2$ | O | —$CH_2$—CH=$CH_2$ | 2 | |
| 5-CON$(CH_3)_2$ | O | —$CH_2$—C($CH_3$)=$CH_2$ | 2 | |
| 5-$COOCH_3$ | O | —$CH_2$—CH=$CH_2$ | 2 | |
| 5-$COOCH_3$ | O | —$CH_2$—C($CH_3$)=$CH_2$ | 2 | |
| H | O | —$CH_2$—CCl=$CH_2$ | 2 | |
| H | O | —$CH_2$—CCl=CH—Cl | 2 | |
| H | O | —$CH_2$—CH=CCl—$CH_3$ | 2 | |
| H | O | —$CH_2$—CH=$CCl_2$ | 2 | |
| 5-$CH_3$ | O | —$CH_2$—CCl=$CH_2$ | 2 | |
| 5-$NO_2$ | O | —$CH_2$—CCl=CH—Cl | 2 | |
| 5-Br | O | —$CH_2$CCl—$CH_2$ | 2 | |
| 5-Cl | O | —$CH_2$—CH=$CCl_2$ | 2 | |
| 5-$C_3H_7$—i | O | —$CH_2$—CH=CCl—$CH_3$ | 2 | |
| 3-$CH_3$ | O | —$CH_2$—CCl=$CH_2$ | 2 | |
| 6-$CH_3$ | O | —$CH_2$CCl—$CH_2$ | 2 | |
| 6-$OCH_3$ | O | —$CH_2$—CCl=CH—Cl | 2 | |
| 5-$OCH_3$ | O | —$CH_2$—CH=$CCl_2$ | 2 | |
| 6-Cl | O | —$CH_2$—CCl=$CH_2$ | 2 | |
| 3-$NO_2$ | O | —$CH_2$—CH=CCl—$CH_3$ | 2 | |
| 3-$CH_3$ | O | —$CH_2$—CH=$CH_2$ | 2 | m.p. 114–116° |
| 3-$NO_2$ | O | —$CH_2$—CH=$CH_2$ | 2 | |
| 3-Cl | O | —$CH_2$—CH=$CH_2$ | 2 | |
| 3-Cl | O | —$CH_2$—CH=CH—$CH_3$ | 2 | |
| 3-Cl | O | —CH—C($CH_3$)=$CH_2$ | 2 | |
| 3-$OCH_3$ | O | —CH—C($CH_3$)=$CH_2$ | 2 | |
| 3-$OCH_3$ | O | —$CH_2$—CH=$CH_2$ | 2 | |
| 2-$OCH_3$ | O | —$CH_2$—CH=$CH_2$ | 5 | m.p. 113–114° |

EXAMPLE 4

(a)

N-[2-(1,2-Dichlorovinyloxy)phenylsulfonyl]-N'-methyl urea

A suspension of 6.7 g of 2-(1,2-dichlorovinyloxy)-phenylsulfonamide in 50 ml of methylene chloride is treated with 1.9 g of methyl isocyanate. 3.3 g of triethylamine are added dropwise to this mixture at a temperature of 20°–25° C. within 10 minutes resulting in a clear solution. The solution is stirred for a further hour and evaporated to dryness. The residue is solved in 5% aqueous sodium carbonate and acidified with a 10% solution of hydrochloric acid yielding 7.8 g of N-[2-(1,2-dichlorovinyloxy)-phenylsulfonyl]-N'-methyl urea, m.p. 225°–226° C.

(b) 2-(1,2-Dichlorovinyloxy)phenylsulfonylisocyanate 9.8 g of N-[2-(1,2-dichlorovinyloxy)phenylsulfonyl]-N'-methyl urea are solved in 200 ml of chlorobenzene. The solution is dried by azeotropic desitlling off of 20 ml of the solvent. 5.3 g of phosgene are introduced into this solution within 45 minutes at a temperature of 120°–130° C. Evaporation of the reaction mixture to dryness yields 8.7 g of 2-(1,2-dichlorovinyloxy)-phenylsulfonylisocyanate in form of a yellowish oil.

(c)

N-[2-(1,2-Dichlorovinyloxy)phenylsulfonyl]-N'-(4-chloro-6-methoxy-pyrimidin-2-yl)urea 7.4 g of 2-(1,2-dichlorovinyloxy)phenylsulfonylisocyanate and 4.0 g of 2-amino-4-chloro-6-methoxypyrimidine are heated to 70°–80° C. in 60 ml of absolute dioxane for 3 hours. After cooling the mixture is treated with activated carbon, filtered and evaporated to 1/5 of the original volume. From the residue crystallise 9.0 g of N-[2-(1,2-Dichlorovinyloxy)phenylsulfonyl]-N'-(4-chloro-6-methoxy-pyrimidin-2-yl)urea, m.p. 196°–198° C.

EXAMPLE 5

N-(2-Allyloxyphenylsulfonyl)-N'-(4,6-dimethylpyrimidin-2-yl)-urea

A mixture of 6.99 g of N-(2-allyloxy-phenylsulfonyl)-phenyl carbamate and 2.46 g of 2-amino-4,6-dimethylpyrimidine are refluxed in 56 ml of dioxane for 45 minutes. The reaction mixture is evaporated to dryness and crystallized from ether yielding 6.0 g of N-(2-allyloxy-phenylsulfonyl)-N'-(4,6-dimethyl-pyrimidin-2-yl)urea, m.p. 199°–200° C.

The compounds of formula I listed in Tables 3 to 6 are obtained in analogous manner:

TABLE 3

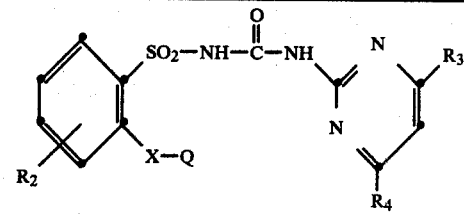

| No. | Q | R$_2$ | R$_3$ | R$_4$ | X | Physical data (°C.) |
|---|---|---|---|---|---|---|
| 1 | —CH$_2$—CH=CH$_2$ | 6-Cl | CH$_3$ | OCH$_3$ | O | m.p. 163–164° |
| 2 | —CH$_2$—CH=CH$_2$ | 6-Cl | OCH$_3$ | OCH$_3$ | O | |
| 3 | —CH$_2$—C(CH$_3$)=CH$_2$ | 6-Cl | CH$_3$ | OCH$_3$ | O | |
| 4 | —CH$_2$—C(CH$_3$)=CH$_2$ | 6-Cl | OCH$_3$ | OCH$_3$ | O | |
| 5 | —CH$_2$—CH=CH—CH$_3$ | 6-Cl | OCH$_3$ | OCH$_3$ | O | |
| 6 | —CH$_2$—CH=CH—CH$_3$ | 6-Cl | OCH$_3$ | CH$_3$ | O | |
| 7 | —CH$_2$—CH=C(CH$_3$)$_2$ | 6-Cl | CH$_3$ | OCH$_3$ | O | |
| 8 | —CH$_2$CH=CH$_2$ | 6-OCH$_3$ | CH$_3$ | OCH$_3$ | O | |
| 9 | —CH$_2$—CH=CH$_2$ | 6-OCH$_3$ | OCH$_3$ | OCH$_3$ | O | |
| 10 | —CH$_2$—C(CH$_3$)=CH$_2$ | 6-OCH$_3$ | OCH$_3$ | OCH$_3$ | O | |
| 11 | —CH$_2$—C(CH$_3$)=CH$_2$ | 6-OCH$_3$ | CH$_3$ | OCH$_3$ | O | |
| 12 | —CH$_2$—CH=C(CH$_3$)$_2$ | 6-Cl | CH$_3$ | OCH$_3$ | O | |
| 13 | —CH—CCl=CH$_2$ | 6-OCH$_3$ | CH$_3$ | OCH$_3$ | O | |
| 14 | —CH—CCl=CH$_2$ | 6-Cl | CH$_3$ | OCH$_3$ | O | |
| 15 | —CH$_2$—CH=CH$_2$ | 6-CH$_3$ | CH$_3$ | OCH$_3$ | O | |
| 16 | —CH$_2$—CH=CH$_2$ | 6-CH$_3$ | OCH$_3$ | OCH$_3$ | O | |
| 17 | —CH$_2$—C(CH$_3$)=CH$_2$ | 6-CH$_3$ | CH$_3$ | OCH$_3$ | O | |
| 18 | —CH$_2$—C(CH$_3$)=CH$_2$ | 6-CH$_3$ | OCH$_3$ | OCH$_3$ | O | |
| 19 | —(CH$_2$)$_2$—CH=CH$_2$ | 6-OCH$_3$ | OCH$_3$ | CH$_3$ | O | |
| 20 | —CH$_2$—CH=CH$_2$ | 6-NO$_2$ | CH$_3$ | OCH$_3$ | O | |
| 21 | —CH$_2$—CH=CH$_2$ | 6-NO$_2$ | OCH$_3$ | OCH$_3$ | O | |
| 22 | —CH$_2$—CH=CH—CH$_3$ | 6-NO$_2$ | OCH$_3$ | OCH$_3$ | O | |
| 23 | —CH$_2$—CH=CH—CH$_3$ | 6-NO$_2$ | OCH$_3$ | CH$_3$ | O | |
| 24 | —CH$_2$—C(CH$_3$)=CH$_2$ | 6-NO$_2$ | OCH$_3$ | CH$_3$ | O | |
| 25 | —CH$_2$—CH=CH$_2$ | 6-COOCH$_3$ | OCH$_3$ | CH$_3$ | O | |
| 26 | —CH$_2$—CH=CH$_2$ | 6-COOCH$_3$ | OCH$_3$ | OCH$_3$ | O | |
| 27 | —CH$_2$CH=CH$_2$ | 5-Cl | CH$_3$ | OCH$_3$ | O | m.p. 197–198° |
| 28 | —CH$_2$—C(CH$_3$)=CH$_2$ | 5-Cl | CH$_3$ | OCH$_3$ | O | |
| 29 | —CH$_2$CH=CH$_2$ | 5-Br | CH$_3$ | OCH$_3$ | O | |
| 30 | —CH—C(CH$_3$)=CH$_2$ | 5-Br | CH$_3$ | OCH$_3$ | O | |
| 31 | —CH$_2$—CH=CH$_2$ | 5-F | CH$_3$ | OCH$_3$ | O | m.p. 200–201° |
| 32 | —CH$_2$—CH=CH$_2$ | 5-F | OCH$_3$ | OCH$_3$ | O | m.p. 162–164° |
| 33 | —CH$_2$—CH=C(CH$_3$)$_2$ | 5-F | CH$_3$ | OCH$_3$ | O | |
| 34 | —CH$_2$—C(CH$_3$)=CH$_2$ | 5-F | CH$_3$ | OCH$_3$ | O | m.p. 197° (decomp.) |
| 35 | —CH$_2$—C(CH$_3$)=CH$_2$ | 5-C$_3$H$_7$—i | CH$_3$ | OCH$_3$ | O | |
| 36 | —CH$_2$—CH=C(CH$_3$)$_2$ | 5-C$_3$H$_7$—i | CH$_3$ | OCH$_3$ | O | |

TABLE 3-continued

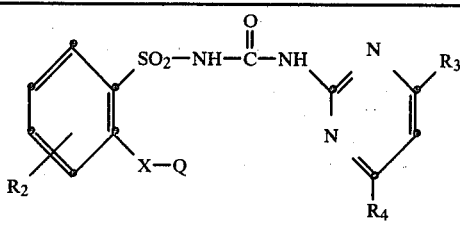

| No. | Q | R₂ | R₃ | R₄ | X | Physical data (°C.) |
|---|---|---|---|---|---|---|
| 37 | —CH₂—CH=CH₂ | 5-C₃H₇—i | CH₃ | OCH₃ | O | m.p. 139–140° |
| 38 | —CH₂—CH=CH₂ | 5-CH₃ | OCH₃ | OCH₃ | O | |
| 39 | —CH₂—CH=CH—CH₃ | 5-CH₃ | OCH₃ | OCH₃ | O | |
| 40 | —CH₂—CH=CH—CH₃ | 5-CH₃ | CH₃ | OCH₃ | O | m.p. 179–182° |
| 41 | —CH₂—CH=CH—CH₃ | 5-NO₂ | CH₃ | OCH₃ | O | |
| 42 | —CH₂—CH=CH₂ | 5-NO₂ | CH₃ | OCH₃ | O | |
| 43 | —CH₂—CH=CH₂ | 5-OCH₃ | CH₃ | OCH₃ | O | m.p. 138–139° |
| 44 | —CH₂—CH=CH₂ | 5-OCH₃ | OCH₃ | OCH₃ | O | |
| 45 | —CH₂—C(CH₃)=CH₂ | 5-OCH₃ | OCH₃ | CH₃ | O | |
| 46 | —CH₂—CH=CH—CH₃ | 5-OCH₃ | OCH₃ | CH₃ | O | |
| 47 | —CH₂—CH=CH—CH₃ | 5-OCH₃ | OCH₃ | OCH₃ | O | |
| 48 | —CH₂—CH=CH₂ | 5-CON(CH₃)₂ | CH₃ | OCH₃ | O | |
| 49 | —CH₂—C(CH₃)=CH₂ | 5-CON(CH₃)₂ | CH₃ | OCH₃ | O | |
| 50 | —CH₂—C(CH₃)=CH₂ | 5-COOCH₃ | CH₃ | OCH₃ | O | |
| 51 | —CH₂—CH=CH₂ | 5-COOCH₃ | CH₃ | OCH₃ | O | |
| 52 | —CH₂—CH=CH₂ | 5-COOCH₃ | OCH₃ | OCH₃ | O | |
| 53 | —CH₂—CCl=CH₂ | 5-CH₃ | OCH₃ | CH₃ | O | |
| 54 | —CH₂—CCl=CH—Cl | 5-NO₂ | OCH₃ | CH₃ | O | |
| 55 | —CH₂—CCl=CH—Cl | 5-Br | OCH₃ | CH₃ | O | |
| 56 | —CH₂—CH=CCl—CH₃ | 5-Cl | CH₃ | OCH₃ | O | |
| 57 | —CH₂—CH=CCl₂ | 5-C₃H₇—i | CH₃ | OCH₃ | O | |
| 58 | —CH₂—CCl=CH₂ | 3-CH₃ | CH₃ | OCH₃ | O | |
| 59 | —CH₂—CCl=CH₂ | 6-CH₃ | CH₃ | OCH₃ | O | |
| 60 | —CH₂—CCl=CH—Cl | 6-OCH₃ | CH₃ | OCH₃ | O | |
| 61 | —CH₂—CH=CCl₂ | 5-OCH₃ | CH₃ | OCH₃ | O | |
| 62 | —CH₂—CCl=CH₂ | 6-Cl | CH₃ | OCH₃ | O | |
| 63 | —CH₂—CH=CH₂ | 3-NO₃ | CH₃ | OCH₃ | O | |
| 64 | —CH₂—C(CH₃)=CH₂ | 3-NO₂ | CH₃ | OCH₃ | O | |
| 65 | —CH₂—C(CH₃)=CH₂ | 3-NO₂ | OCH₃ | OCH₃ | O | |
| 66 | —CH₂—CH=CCl—CH₃ | 3-NO₂ | OCH₃ | OCH₃ | O | |
| 67 | —CH₂—CH=CCl—CH₃ | 3-NO₂ | OCH₃ | CH₃ | O | |
| 68 | —CH₂—CH=CH₂ | 3-CH₃ | OCH₃ | CH₃ | O | m.p. 163–164° |
| 69 | —CH₂—CH=CH₂ | 3-CH₃ | OCH₃ | CH₃ | O | |
| 70 | —CH₂—CH=CH₂ | 3-Cl | OCH₃ | CH₃ | O | |
| 71 | —CH₂—CH=CH₂ | 3-Cl | OCH₃ | OCH₃ | O | |
| 72 | —CH₂—C(CH₃)=CH₂ | 3-Cl | OCH₃ | CH₃ | O | |
| 73 | —CH₂—CH=CH—CH₃ | 3-Cl | CH₃ | OCH₃ | O | |
| 74 | —CH₂—C(CH₃)=CH₂ | 3-OCH₃ | CH₃ | OCH₃ | O | |
| 75 | —CH₂—CH=CH₂ | 3-OCH₃ | CH₃ | OCH₃ | O | |
| 76 | —CH₂—CH=CH₂ | 3-OCH₃ | OCH₃ | OCH₃ | O | |

TABLE 4

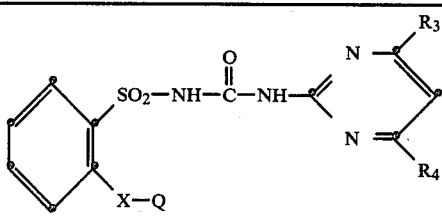

| No. | Q | R₃ | R₄ | X | Physical data (°C.) |
|---|---|---|---|---|---|
| 101 | —CH₂—C(CH₃)=CH₂ | CH₃ | OCH₃ | O | m.p. 172–177° |
| 102 | —CH₂—C(CH₃)=CH₂ | OCH₃ | OCH₃ | O | |
| 103 | —CH₂—C(CH₃)=CH₂ | CH₃ | CH₃ | O | |
| 104 | —CH₂—C(CH₃)=CH₂ | C₂H₅ | OCH₃ | O | |
| 105 | —CH₂—C(CH₃)=CH₂ | OCH₃ | Cl | O | m.p. 179–180° |
| 106 | —CH₂—C(CH₃)=CH₂ | CH₃ | Cl | O | |
| 107 | —CH₂—C(CH₃)=CH₂ | CF₃ | OCH₃ | O | |
| 108 | —CH₂—C(CH₃)=CH₂ | —CH₂—OCH₃ | OCH₃ | O | |
| 109 | —CH₂—O(CH₃)=CH₂ | Br | OCH₃ | O | |
| 110 | —CH₂—C(CH₃)=CH₂ | Br | CH₃ | O | |
| 111 | —CH₂—C(CH₃)=CH₂ | OCH₃ | SCH₃ | O | |
| 112 | —CH₂—C(CH₃)=CH₂ | CH₃ | SCH₃ | O | |

TABLE 4-continued

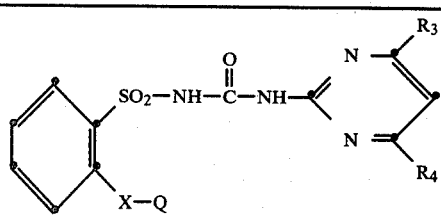

| No. | Q | R$_3$ | R$_4$ | X | Physical data (°C.) |
|---|---|---|---|---|---|
| 113 | —CH$_2$—C(CH$_3$)=CH$_2$ | OCH$_3$ | OC$_2$H$_5$ | O | |
| 114 | —CH$_2$—CH=CH—CH$_3$ | CH$_3$ | OCH$_3$ | O | m.p. 185–186° |
| 115 | —CH$_2$—CH=CH—CH$_3$ | OCH$_3$ | OCH$_3$ | O | |
| 116 | —CH$_2$—CH=CH—CH$_3$ | CH$_3$ | CH$_3$ | O | |
| 117 | —CH$_2$—CH=CH—CH$_3$ | —CH$_2$—OCH$_3$ | OCH$_3$ | O | |
| 118 | —CH$_2$—CH=CH—CH$_3$ | CH$_3$ | Cl | O | |
| 119 | —CH$_2$—CH=CH—CH$_3$ | OCH$_3$ | Cl | O | m.p. 193–195° |
| 120 | —CH$_2$—CH=CH—CH$_3$ | OCH$_3$ | OC$_2$H$_5$ | O | |
| 121 | —CH$_2$—CH=C(CH$_3$)$_2$ | CH$_3$ | OCH$_3$ | O | |
| 122 | —CH$_2$—CH=C(CH$_3$)$_2$ | OCH$_3$ | OCH$_3$ | O | |
| 123 | —CH$_2$—CH=C(CH$_3$)$_2$ | CH$_3$ | CH$_3$ | O | |
| 124 | —CH$_2$—CH=C(CH$_3$)$_2$ | OCH$_3$ | Cl | O | |
| 125 | —CH$_2$—CH=C(CH$_3$)$_2$ | CH$_3$ | Cl | O | |
| 126 | —CH$_2$—CH=C(CH$_3$)$_2$ | OCH$_3$ | OC$_2$H$_5$ | O | |
| 127 | —CH$_2$—CCl=CH$_2$ | CH$_3$ | OCH$_3$ | O | |
| 128 | —CH$_2$—CCl=CH$_2$ | OCH$_3$ | OCH$_3$ | O | |
| 129 | —CH$_2$—CCl=CH$_2$ | CH$_3$ | CH$_3$ | O | |
| 130 | —CH$_2$—CCl=CH$_2$ | OCH$_3$ | Cl | O | |
| 131 | —CH$_2$—CCl=CH$_2$ | CH$_3$ | Cl | O | |
| 132 | —CH$_2$—CCl=CH$_2$ | OC$_2$H$_5$ | OCH$_3$ | O | |
| 133 | —CH$_2$—CCl=CH$_2$ | —CH$_2$—OCH$_3$ | OCH$_3$ | O | |
| 134 | —CH$_2$—CCl=CH$_2$ | C$_2$H$_5$ | OCH$_3$ | O | |
| 135 | —CH$_2$—CH=C(CH$_3$)$_2$ | C$_2$H$_5$ | OCH$_3$ | O | |
| 136 | —CH$_2$—CH=CH—CH$_3$ | C$_2$H$_5$ | OCH$_3$ | O | |
| 137 | —(CH$_2$)$_2$—CH=CH$_2$ | CH$_3$ | OCH$_3$ | O | |
| 138 | —(CH$_2$)$_2$—CH=CH$_2$ | CH$_3$ | CH$_3$ | O | |
| 139 | —(CH$_2$)$_3$—CH=CH$_2$ | CH$_3$ | OCH$_3$ | O | |
| 140 | —CH(CH$_3$)—CH=CH$_2$ | CH$_3$ | OCH$_3$ | O | |
| 141 | —CH$_2$—CCl=CH—Cl | CH$_3$ | OCH$_3$ | O | |
| 142 | —CH$_2$—CH=CCl—CH$_3$ | CH$_3$ | OCH$_3$ | O | |
| 143 | —CH$_2$—CH=CCl$_2$ | CH$_3$ | OCH$_3$ | O | |
| 144 | —CCl=CHCl | OCH$_3$ | OCH$_3$ | O | m.p. 244–246° |
| 145 | —CCl=CCl$_2$ | CH$_3$ | OCH$_3$ | O | |
| 146 | —CCl=CCl$_2$ | OCH$_3$ | OCH$_3$ | O | |
| 147 | —CCl=CCl$_2$ | CH$_3$ | Cl | O | |
| 148 | —CF=CF$_2$ | CH$_3$ | Cl | O | |
| 149 | —CH=CCl$_2$ | CH$_3$ | OCH$_3$ | O | |
| 150 | —CH=CCl$_2$ | OCH$_3$ | OCH$_3$ | O | |
| 151 | —CCl=CHCl | OCH$_3$ | Cl | O | m.p. 196–198° |
| 152 | —CCl=CHCl | C$_2$H$_5$ | OCH$_3$ | O | |
| 153 | —CCl=CHCl | CH$_3$ | Cl | O | |
| 154 | —CCl=CHCl | CH$_3$ | OCH$_3$ | S | |
| 155 | —CCl=CHCl | OCH$_3$ | OCH$_3$ | S | |
| 156 | —CF=CF$_2$ | CH$_3$ | OCH$_3$ | O | |
| 157 | —CF=CF$_2$ | OCH$_3$ | OCH$_3$ | O | |
| 158 | —CH$_2$—CH=CH$_2$ | —CH(CH$_3$)$_2$ | OCH$_3$ | O | |
| 159 | —CH$_2$—CH=CH$_2$ | OCH$_3$ | SC$_2$H$_5$ | O | |
| 160 | —CH$_2$—CH=CH$_2$ | OC$_2$H$_5$ | OC$_2$H$_5$ | O | |
| 161 | —CH$_2$—CH=CH$_2$ | CH$_3$ | CH$_3$ | O | m.p. 180–182° |
| 162 | —CH$_2$—CH=CH$_2$ | CH$_3$ | OCH$_3$ | O | m.p. 98–100° |
| 163 | —CH$_2$—CH=CH$_2$ | C$_2$H$_5$ | Cl | O | |
| 164 | —CH$_2$—CH=CH$_2$ | CH$_3$ | Cl | O | m.p. 153–154° |
| 165 | —CH$_2$—CH=CH$_2$ | CH$_3$ | SCH$_3$ | O | |
| 166 | —CH$_2$—CH=CH$_2$ | CH$_3$ | F | O | |
| 167 | —CH$_2$—CH=CH$_2$ | CH$_3$ | Br | O | |
| 168 | —CH$_2$—CH=CH$_2$ | C$_2$H$_5$ | OC$_2$H$_5$ | O | |
| 169 | —CH$_2$—CH=CH$_2$ | C$_2$H$_5$ | SCH$_3$ | O | |
| 170 | —CH$_2$—CH=CH$_2$ | CF$_3$ | CH$_3$ | O | |
| 171 | —CH$_2$—CH=CH$_2$ | CH$_2$Cl | CH$_3$ | O | |
| 172 | —CH$_2$—CH=CH$_2$ | CH$_2$Cl | OCH$_3$ | O | |
| 173 | —CH$_2$—CH=CH$_2$ | OCH$_3$ | Cl | O | m.p. 173–179° |
| 174 | —CH$_2$—CH=CH$_2$ | Cl | Cl | O | |
| 175 | —CH$_2$—CH=CH$_2$ | OCH$_3$ | SCH$_3$ | O | |
| 176 | —CH$_2$—CH=CH$_2$ | OCH$_3$ | —OC$_3$H$_7$—i | O | |
| 177 | —CH$_2$—CH=CH$_2$ | CH$_2$F | OCH$_3$ | O | |
| 178 | —CH$_2$—CH=CH$_2$ | CH$_2$F | CH$_3$ | O | |
| 179 | —CH$_2$—CH=CH$_2$ | CF$_3$ | OCH$_3$ | O | |
| 180 | —CH$_2$—CH=CH$_2$ | OCH$_3$ | OCH$_3$ | O | |
| 181 | —CH$_2$—CH=CH$_2$ | OCH$_3$ | OC$_2$H$_5$ | O | |

TABLE 4-continued

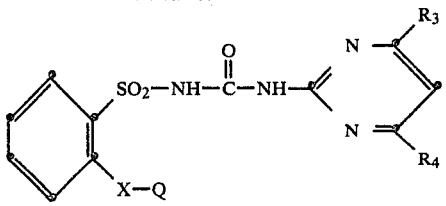

| No. | Q | $R_3$ | $R_4$ | X | Physical data (°C.) |
|---|---|---|---|---|---|
| 182 | —$CH_2$—CH=$CH_2$ | $CH_2OCH_3$ | $OCH_3$ | O | |
| 183 | —$CH_2$—CH=$CH_2$ | $C_2H_5$ | $OCH_3$ | O | |
| 184 | —CCl=CHCl | $CH_3$ | $OCH_3$ | O | m.p. 208–209° |

TABLE 5

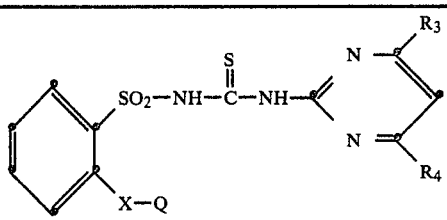

| No. | Q | $R_3$ | $R_4$ | X |
|---|---|---|---|---|
| 200 | —$CH_2$—C($CH_3$)=$CH_2$ | $CH_3$ | $OCH_3$ | O |

TABLE 6

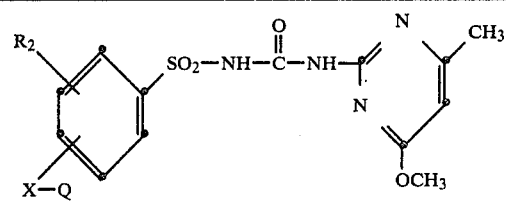

| No. | Q | Position | $R_2$ | X |
|---|---|---|---|---|
| 250 | —$CH_2$—CH=$CH_2$ | 5 | 2-$CH_3$ | O |
| 251 | —$CH_3$—C($CH_3$)=$CH_2$ | 5 | 2-$CH_3$ | O |
| 252 | —$CH_2$—CH=CH—$CH_3$ | 5 | 2-$CH_3$ | O |
| 253 | —$CH_2$—CCl=$CH_2$ | 5 | 2-$CH_3$ | O |
| 254 | —$CH_2$—CH=$CH_2$ | 5 | 2-Cl | O |
| 255 | —$CH_2$—CCl=$CH_2$ | 5 | 2-Cl | O |
| 256 | —$CH_2$—C($CH_3$)=$CH_2$ | 5 | 2-Cl | O |
| 257 | —$CH_2$—CH=CH—$CH_3$ | 5 | 2-Cl | O |
| 258 | —$CH_2$—CH=$CH_2$ | 3 | 2-$CH_3$ | O |
| 259 | —$CH_2$—C($CH_3$)=$CH_3$ | 3 | 2-$CH_3$ | O |
| 260 | —$CH_2$—CH=$CH_2$ | 3 | 2-$OCH_3$ | O |
| 261 | —$CH_2$—C($CH_3$)=$CH_2$ | 3 | 2-$OCH_3$ | O |
| 262 | —$CH_2CCl$=$CH_2$ | 3 | 2-$OCH_3$ | O |
| 263 | —$CH_2$—CH=CH—$CH_3$ | 3 | 2-$OCH_3$ | O |
| 264 | —$CH_2$—CH=$CH_2$ | 5 | 2-$OCH_3$ | O |
| 265 | —$CH_2$—C($CH_3$)=$CH_2$ | 5 | 2-$OCH_3$ | O |
| 266 | —$CH_2$—CH=CH—$CH_3$ | 5 | 2-$OCH_3$ | O |
| 267 | —$CH_2$—CCl=$CH_2$ | 5 | 2-$OCH_3$ | O |

FORMULATION EXAMPLES

EXAMPLE 6

Formulation examples for active ingredients of the formula I (throughout, percentages are by weight)

| (a) Wettable powders | (a) | (b) | (c) |
|---|---|---|---|
| active ingredient | 20% | 60% | 0.5% |
| sodium lignosulfonate | 5% | 5% | 5% |

-continued

| (a) Wettable powders | (a) | (b) | (c) |
|---|---|---|---|
| sodium laurylsulfate | 3% | — | — |
| sodium diisobutylnaphthalene-sulfonate | — | 6% | 6% |
| octylphenol polyethylene glycol ether (7–8 moles of ethylene oxide | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| active ingredient | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 3% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| active ingredient | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| active ingredient | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| active ingredient | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| active ingredient | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| active ingredient | 5% |
| isopropylamine | 1% |
| octylphenol polyethylene glycol ether (78 moles of ethylene oxide) | 3% |
| water | 91% |

BIOLOGICAL EXAMPLES

EXAMPLE 7

Preemergence herbicidal action

In a greenhouse, plant seeds are sown in flower pots of 12-15 cm diameter. Immediately after sowing, the surface of the soil is treated with an aqueous dispersion or solution of the compounds to be tested. Concentrations of 4 kg a.i./ha are employed. The pots are then kept in the greenhouse at 22°-25° C. and 50-70% relative humidity. The test is evaluated 3 weeks later in accordance with the following rating:
1 = plants totally withered
2-3 = very pronounced action
4-6 = medium action
7-8 = insignificant action
9 = no action (as untreated controls).

EXAMPLE 8

Postemergence herbicidal action (contact action)

A number of weeds and cultivated plants in pots, both monocots and dicots, are sprayed postemergence, in the 4- to 6-leaf stage, with an aqueous active ingredient dispersion at a rate of application of 4 kg a.i./ha, and then kept at 24°-26° C. and 45-60% relative humidity. The test is evaluated 15 days after treatment and the action is assessed in accordance with the same rating as in Example 6.

EXAMPLE 9

Inhibition of sprouting in stored potatoes

A number of commercially available potatoes of the "Urgenta" variety, without sprouts, are washed and dried. The potatoes are then immersed in emulsions of the compounds to be tested in different concentrations, placed on filter paper in plastic dishes, and kept in the dark at 14°-21° C. and 50% relative humidity. Evaluation is made 34 days after application.

The percentage weight loss of the tubers and the weight of the sprouts compared with untreated controls are simultaneously determined. A number of the compounds of formula I inhibited sprouting completely in this test. At the same time, the weight loss of the potatoes was less than 10% of the weight loss of the control potatoes.

EXAMPLE 10

Growth inhibition of tropical cover crops

The test plants (centrosema plumieri and centrosema pubescens) are reared until fully grown and then cut back to a height of 60 cm. The plants are sprayed 7 days later with an aqueous emulsion of the compound to be tested. The test plants are kept at 70% relative humidity and 6000 lux artificial light for 14 hours per day, at day temperatures of 27° C. and night temperatures of 21° C. The test is evaluated 4 weeks after application.

The new growth in comparison with the control is assessed and the phytotoxicity is determined. In this test, new growth of plants treated with a number of compounds of the formula I is markedly reduced (less than 20%), without damage being caused to the test plants.

What is claimed is:

1. A N-phenylsulfonyl-N'-pyrimidinyl-urea of the formula I

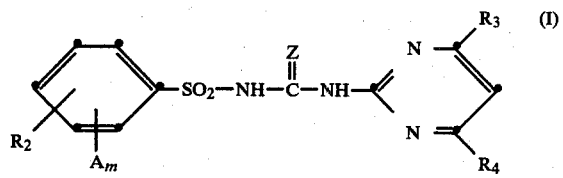

wherein
A is a $C_2$-$C_6$ alkenyloxy, $C_2$-$C_6$ haloalkenyloxy, $C_2$-$C_6$ haloalkenylthio, $C_2$-$C_6$ haloalkenylsulfinyl or $C_2$-$C_6$ haloalkenylsulfonyl radical
Z is oxygen or sulfur,
m is 1 or 2,
$R_2$ is hydrogen, halogen, $C_1$-$C_5$alkyl, $C_2$-$C_5$alkenyl, $C_1$-$C_4$-haloalkyl, or a radical —Y—$R_5$, —COO$R_6$, —NO$_2$ or —CO—N$R_7$—$R_8$,
$R_3$ and $R_4$, each independently of the other, are hydrogen, $C_1$-$C_4$alkyl, $C_1$-$C_4$alkoxy, $C_1$-$C_4$alkylthio, $C_1$-$C_4$haloalkyl, halogen or alkoxyalkyl of at most 4 carbon atoms,
$R_5$ and $R_6$, each independently of the other, are $C_1$-$C_5$alkyl, $C_2$-$C_5$alkenyl or $C_2$-$C_6$alkynyl,
$R_7$ and $R_8$, each independently of the other, are hydrogen, $C_1$-$C_5$alkyl, $C_2$-$C_5$alkenyl or $C_2$-$C_6$alkynyl, and
Y is oxygen, sulfur, a sulfinyl or sulfonyl bridge, or a salt thereof.

2. A compound according to claim 1, wherein Z is oxygen.

3. A compound according to claim 1, wherein $R_3$ and $R_4$ together contain not more than 4 carbon atoms.

4. A compound according to claim 1, wherein Z is oxygen and m is 1.

5. A compound according to claim 1, wherein Z is oxygen and m is 2.

6. A compound according to claim 4, wherein the radical —A is in the 2- or 3-position to the sulfonyl group.

7. A compound according to claim 6, wherein the radical —A is in the 2-position.

8. A compound according to claim 5, wherein both radicals —A are in the 2- and 5-position to the sulfonyl group.

9. A compound according to claim 2, wherein only one radical —A is in the 2-position to the sulfonyl radical and $R_3$ and $R_4$ together contain not more than 4 carbon atoms.

10. A compound according to claim 2, wherein two radicals —A are in the 2- and 5-position to the sulfonyl radical and $R_3$ and $R_4$ together contain not more than 4 carbon atoms.

11. A compound according to claim 9, wherein $R_2$ is in the 5- or 6-position to the sulfonyl group.

12. A compound according to claim 11, wherein $R_2$ is hydrogen, halogen, $C_1$-$C_4$alkoxy, nitro or —$COOR_6$.

13. A compound according to claim 12, wherein $R_2$ is hydrogen, fluorine, nitro or $C_1$-$C_4$alkoxy and each of $R_3$ and $R_4$ is hydrogen, $C_1$-$C_4$alkoxy, $C_1$-$C_4$alkylthio, halogen or alkoxyalkyl, whilst $R_3$ and $R_4$ together contain at most 4 carbon atoms.

14. A compound according to claim 13, wherein $R_2$ is hydrogen, and each of $R_3$ and $R_4$ is $C_1$-$C_4$alkyl, $C_1$-$C_4$alkoxy, methylthio, halogen, or alkoxyalkyl.

15. A compound according to claim 15, wherein A is $C_2$-$C_4$haloalkenyloxy or $C_2$-$C_6$alkenyloxy.

16. A compound according to claim 15, wherein A is $C_2$-$C_6$alkenyloxy and each of $R_3$ and $R_4$ is methyl, ethyl, chlorine or methoxy.

17. A compound according to claim 15, wherein A is vinyloxy substituted by 1 to 3 halogen atoms, and each of $R_3$ and $R_4$ is methyl, ethyl, chlorine or methoxy.

18. A compound according to claim 1, wherein Z is sulfur, each of $R_3$ and $R_4$ independently is $C_1$-$C_3$alkyl, $C_1$-$C_3$alkoxy or $C_1$-$C_3$alkylthio, containing together at most 4 carbon atoms, and A is —O—CCl=CHCl, and the radical —A is in the 2-position and m is 1.

19. N-[2-(1,2-Dichlorovinyloxy)-phenylsulfonyl]-N'-(4-chloro-6-methoxy-pyrimidin-2-yl)-urea according to claim 1.

20. A herbicidal and growth regulating composition which comprises an effective amount of at least one compound according to claim 1, together with a suitable carrier thereof.

21. A method of controlling undesired plant growth, which method comprises applying thereto or to the locus thereof a herbicidally effective amount of a compound according to claim 1.

22. A method of suppressing plant growth, which method comprises applying thereto or to the locus thereof an effective amount of a compound according to claim 1.

23. A method according to claim 21 for selectively controlling weeds in crops of cultivated plants which method comprises applying the compound according to claim 1 preemergence or postemergence.

24. A method according to claim 21 for suppressing plant growth beyond the two-leaf-stage which method comprises applying the compound according to claim 1 preemergence.

* * * * *